United States Patent
Pic et al.

(10) Patent No.: US 12,337,139 B2
(45) Date of Patent: Jun. 24, 2025

(54) MEDICAL DEVICES FOR AGENT DELIVERY AND RELATED METHODS OF USE

(71) Applicant: Boston Scientific Scimed, Inc., Maple Grove, MN (US)

(72) Inventors: Andrew Pic, Northboro, MA (US); Collin Murray, Maynard, MA (US); Laurie A. Lehtinen, Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 644 days.

(21) Appl. No.: 17/109,434

(22) Filed: Dec. 2, 2020

(65) Prior Publication Data

US 2021/0162122 A1    Jun. 3, 2021

Related U.S. Application Data

(60) Provisional application No. 62/943,060, filed on Dec. 3, 2019.

(51) Int. Cl.
*A61M 39/24* (2006.01)
*A61M 5/155* (2006.01)
*A61M 5/168* (2006.01)

(52) U.S. Cl.
CPC ........ *A61M 5/155* (2013.01); *A61M 5/16804* (2013.01); *A61M 39/24* (2013.01);
(Continued)

(58) Field of Classification Search
CPC ...... A61M 11/02; A61M 5/155; A61M 39/24; A61M 5/16804; A61M 2202/064;
(Continued)

(56) References Cited

U.S. PATENT DOCUMENTS

| 471,854 A | 3/1892 | Howard |
| 881,238 A | 3/1908 | Hasbrouck |

(Continued)

FOREIGN PATENT DOCUMENTS

| CN | 101401956 B | 11/2012 |
| DE | 60215438 T2 | 8/2007 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Shefali D Patel
*Assistant Examiner* — William R Frehe
(74) *Attorney, Agent, or Firm* — Bookoff McAndrews, PLLC (57) ABSTRACT

A device may be configured to deliver an agent to a target tissue via a pressurized fluid and the device may include a catheter including a lumen; an enclosure configured to store the agent, receive the pressurized fluid, and release a combination of the pressurized fluid and the agent; and a valve downstream of the enclosure to receive the combination of the pressurized fluid and the agent from the enclosure. The valve may have a first configuration preventing a flow of the combination through the lumen and a second configuration permitting the flow of the combination through the lumen.

20 Claims, 4 Drawing Sheets

(52) U.S. Cl.
CPC . *A61M 2039/248* (2013.01); *A61M 2202/064* (2013.01); *A61M 2205/75* (2013.01); *A61M 2210/1042* (2013.01)

(58) Field of Classification Search
CPC .......... A61M 2210/1042; A61M 3/005; A61M 5/2066; A61M 5/2448; A61M 5/284; A61M 5/31596; A61M 5/3294; A61M 2039/0027; A61M 5/1407; A61M 5/1409; A61M 5/142; A61M 5/145; A61M 5/1452; A61M 5/16827; A61M 25/0075; A61M 25/0097; A61M 39/22; A61M 2039/226; A61M 2039/2473; A61M 2039/2486; A61B 2017/00818; A61B 17/00491; A61B 2017/00522; A61B 2017/00544; F16K 31/5245
See application file for complete search history.

(56) References Cited

U.S. PATENT DOCUMENTS

| | | |
|---|---|---|
| 1,145,520 A | 7/1915 | Smith |
| 1,599,959 A | 9/1926 | Buheiji |
| 1,732,566 A | 10/1929 | McKendrick |
| 1,933,740 A | 11/1933 | Gompei |
| 2,021,587 A | 11/1935 | Agner |
| 2,151,418 A | 3/1939 | Bolté |
| 2,185,927 A | 6/1940 | Shelanski |
| 2,478,715 A | 8/1949 | Schmitt |
| 2,623,519 A | 12/1952 | Cohen |
| 3,669,113 A | 6/1972 | Altounyan et al. |
| 3,940,061 A | 2/1976 | Gimple et al. |
| 4,184,258 A | 6/1980 | Barrington et al. |
| 4,427,450 A | 1/1984 | Kostansek |
| 4,457,329 A | 7/1984 | Werley et al. |
| 4,806,167 A | 2/1989 | Raythatha |
| 5,215,221 A | 6/1993 | Dirksing |
| 5,231,983 A | 8/1993 | Matson et al. |
| 5,273,531 A | 12/1993 | Knoepfler |
| 5,312,331 A | 5/1994 | Kneopfler |
| 5,312,333 A | 5/1994 | Churinetz et al. |
| 5,366,122 A | 11/1994 | Guentert et al. |
| 5,445,612 A | 8/1995 | Terakura et al. |
| 5,470,311 A | 11/1995 | Setterstrom et al. |
| 5,884,621 A | 3/1999 | Matsugi et al. |
| 5,951,531 A | 9/1999 | Ferdman et al. |
| 6,003,512 A | 12/1999 | Gerde |
| 6,484,750 B1 | 11/2002 | Foos et al. |
| 6,554,022 B2 | 4/2003 | Wakeman |
| 6,589,087 B2 | 7/2003 | Mackal et al. |
| 6,684,917 B2 | 2/2004 | Zhu et al. |
| 6,708,712 B2 | 3/2004 | Wakeman |
| 6,716,190 B1 | 4/2004 | Glines et al. |
| 6,799,571 B1 | 10/2004 | Hughes et al. |
| 7,178,547 B2 | 2/2007 | Mackal |
| 7,311,270 B2 | 12/2007 | Kapila |
| 7,334,598 B1 | 2/2008 | Hollars |
| 7,361,300 B2 | 4/2008 | Kelly et al. |
| 7,427,607 B2 | 9/2008 | Suzuki |
| 7,455,248 B2 | 11/2008 | Kablik et al. |
| 7,461,649 B2 | 12/2008 | Gamard et al. |
| 7,544,177 B2 | 6/2009 | Gertner |
| 7,563,299 B2 | 7/2009 | Baptista da Costa et al. |
| 7,673,647 B2 | 3/2010 | Mackal |
| 7,841,338 B2 | 11/2010 | Dunne et al. |
| 7,892,205 B2 | 2/2011 | Palasis et al. |
| 7,921,874 B2 | 4/2011 | Tekulve et al. |
| 8,037,880 B2 | 10/2011 | Zhu et al. |
| 8,097,071 B2 | 1/2012 | Burgess et al. |
| 8,118,777 B2 | 2/2012 | Ducharme et al. |
| 8,269,058 B2 | 9/2012 | McCarthy et al. |
| 8,313,474 B2 | 11/2012 | Campbell et al. |
| 8,360,276 B2 | 1/2013 | Rogier et al. |
| 8,361,054 B2 | 1/2013 | Ducharme et al. |
| 8,496,189 B2 | 7/2013 | Lomond et al. |
| 8,673,065 B2 | 3/2014 | Burgess et al. |
| 8,721,582 B2 | 5/2014 | Ji |
| 8,728,032 B2 | 5/2014 | Ducharme et al. |
| 8,741,335 B2 | 6/2014 | McCarthy |
| 8,827,980 B2 | 9/2014 | Ji |
| 8,910,627 B2 | 12/2014 | Iwatschenko et al. |
| 8,951,565 B2 | 2/2015 | McCarthy |
| 9,028,437 B2 | 5/2015 | Ott et al. |
| 9,089,658 B2 | 7/2015 | Dunne et al. |
| 9,101,744 B2 | 8/2015 | Ducharme |
| 9,107,668 B2 | 8/2015 | Melsheimer et al. |
| 9,132,206 B2 | 9/2015 | McCarthy |
| 9,204,957 B2 | 12/2015 | Gregory et al. |
| 9,205,170 B2 | 12/2015 | Lucchesi et al. |
| 9,205,207 B2 | 12/2015 | Ji |
| 9,205,240 B2 | 12/2015 | Greenhalgh et al. |
| 9,308,584 B2 | 4/2016 | Burgess et al. |
| 9,310,812 B2 | 4/2016 | Costle et al. |
| 9,375,533 B2 | 6/2016 | Ducharme et al. |
| 9,492,646 B2 | 11/2016 | Hoogenakker et al. |
| 9,517,976 B2 | 12/2016 | Mackal |
| 9,545,490 B2 | 1/2017 | Iwatschenko et al. |
| 9,555,185 B2 | 1/2017 | Foster et al. |
| 9,629,966 B2 | 4/2017 | Ji |
| 9,636,470 B2 | 5/2017 | Pohlmann et al. |
| 9,707,359 B2 | 7/2017 | Kubo |
| 9,713,682 B2 | 7/2017 | Eistetter et al. |
| 9,717,897 B2 | 8/2017 | Rogier |
| 9,821,084 B2 | 11/2017 | Diegelmann et al. |
| 9,839,772 B2 | 12/2017 | Ducharme |
| 9,839,774 B2 | 12/2017 | Bonaldo |
| 9,846,439 B2 | 12/2017 | Carman et al. |
| 9,867,931 B2 | 1/2018 | Gittard |
| 9,976,660 B2 | 5/2018 | Stanton et al. |
| 10,004,690 B2 | 6/2018 | Lee et al. |
| 10,010,705 B2 | 7/2018 | Greenhalgh et al. |
| 10,017,231 B2 | 7/2018 | Fawcett, Jr. |
| 10,036,617 B2 | 7/2018 | Mackal |
| 10,065,004 B2 | 9/2018 | Eder et al. |
| 10,173,019 B2 | 1/2019 | Kaufmann et al. |
| 10,384,049 B2 | 8/2019 | Stanton et al. |
| 10,463,811 B2 | 11/2019 | Lee et al. |
| 10,507,293 B2 | 12/2019 | Goodman et al. |
| 10,646,706 B2 | 5/2020 | Rogier |
| 10,730,595 B2 | 8/2020 | Fawcett |
| 10,751,523 B2 | 8/2020 | Rogier |
| 10,806,853 B2 | 10/2020 | Gittard |
| 10,850,814 B2 | 12/2020 | Fawcett |
| 10,994,818 B2 | 5/2021 | Hernandez |
| 2003/0178440 A1* | 9/2003 | Wright ............ A61M 15/0028 222/541.2 |
| 2004/0107963 A1 | 6/2004 | Finlay et al. |
| 2004/0249359 A1 | 12/2004 | Palasis et al. |
| 2005/0121025 A1 | 6/2005 | Gamard et al. |
| 2005/0124932 A1 | 6/2005 | Foster et al. |
| 2005/0147656 A1 | 7/2005 | McCarthy et al. |
| 2005/0220721 A1 | 10/2005 | Kablik et al. |
| 2006/0004314 A1 | 1/2006 | McCarthy et al. |
| 2006/0213514 A1 | 9/2006 | Price et al. |
| 2007/0056586 A1 | 3/2007 | Price et al. |
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0083137 A1 | 8/2007 | Hopman et al. |
| 2007/0199824 A1 | 8/2007 | Hoerr et al. |
| 2008/0021374 A1 | 1/2008 | Kawata |
| 2008/0287907 A1 | 11/2008 | Gregory et al. |
| 2009/0101144 A1 | 4/2009 | Gamard et al. |
| 2009/0112255 A1 | 4/2009 | Leopold et al. |
| 2009/0155342 A1 | 6/2009 | Diegemann et al. |
| 2009/0281486 A1 | 11/2009 | Ducharme |
| 2010/0121261 A1 | 5/2010 | Kablik et al. |
| 2010/0305505 A1 | 12/2010 | Ducharme et al. |
| 2011/0073200 A1 | 3/2011 | Overvaag et al. |
| 2011/0274726 A1 | 11/2011 | Guo et al. |
| 2011/0308516 A1 | 12/2011 | Price et al. |

(56) References Cited

U.S. PATENT DOCUMENTS

| | | | |
|---|---|---|---|
| 2013/0110080 A1* | 5/2013 | Ducharme | A61M 5/155 604/506 |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2015/0233485 A1* | 8/2015 | Cheng | F16K 1/52 251/113 |
| 2016/0250011 A1 | 9/2016 | Sergi | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1* | 7/2018 | Smith | A61M 13/00 |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |
| 2019/0232030 A1* | 8/2019 | Pic | A61B 17/00491 |
| 2021/0024187 A1 | 1/2021 | Fawcett et al. | |
| 2021/0069485 A1 | 3/2021 | Rogier | |

FOREIGN PATENT DOCUMENTS

| | | |
|---|---|---|
| EP | 3052168 B1 | 11/2019 |
| JP | H07118305 A | 5/1995 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2015050814 A1 | 4/2015 |
| WO | 2018157772 A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

Retsch GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion issued in related PCT/US2020/062845, dated Feb. 24, 2021 (English, 13 pages).

* cited by examiner

MEDICAL DEVICES FOR AGENT DELIVERY AND RELATED METHODS OF USE

CROSS-REFERENCE TO RELATED APPLICATIONS

This patent application claims the benefit under 35 U.S.C. § 119 to U.S. Provisional Patent Application No. 62/943,060, filed on Dec. 3, 2019, the entirety of which is incorporated herein by reference.

TECHNICAL FIELD

The present disclosure relates generally to medical systems and devices for delivering pressurized fluids/agents, and more particularly, to methods and tools for controlling delivery of the fluid/agent at an appropriate pressure and flow rate.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY OF THE DISCLOSURE

Examples of the present disclosure relate to, among other things, agent delivery devices. Each of the examples disclosed herein may include one or more of the features described in connection with the disclosed examples.

A device may be configured to deliver an agent to a target tissue via pressurized fluid and the device may include a catheter including a lumen; an enclosure configured to store an agent, receive a pressurized fluid, and release a combination of the pressurized fluid and the agent; and a valve downstream of the enclosure to receive the combination of the pressurized fluid and the agent from the enclosure. The valve may have a first configuration preventing flow of the combination through the lumen and a second configuration permitting flow of the combination through the lumen.

Any of the systems and devices disclosed herein may have any of the following features. A first fluid input may be configured to release pressurized fluid from a pressurized fluid container into the lumen upon coupling the container to the first fluid input. The valve may be within a housing, and the housing may include a handle. The agent may be a powdered medicament. The valve may include a chamber, and the chamber may be fluidically connected to the lumen via an output channel. The valve may also include a rod including a plunger at a distal end of the rod, and the rod may extend through the chamber and may be configured to prevent fluid flow to the output channel in a first configuration and to allow fluid flow to the output channel in a second configuration. The valve may further include a slider slidably coupled to the chamber and including a slot, and the rod may extend through the slot, and the slider may be configured to transition the valve from a first configuration to a second configuration by movement of the slider. The valve may also include a biasing member coupled to the rod, and the biasing member may be configured to bias the rod towards the first configuration of the valve. The slider may include a slide on which the rod rests, the slide having a first portion including a curved surface and a second portion including a planar surface. The rod may include an end extending radially outward relative to an adjacent portion of the rod, and wherein the end of the rod prevents the rod from moving through the slot when the end of the rod contacts the slider. The end of the rod may slidably engage the slider.

The valve may include a chamber, and the chamber may be fluidically connected to the lumen via an output channel. The valve may also include a rod including a plunger at a first end of the rod and a cam-engaging surface at a second end of the rod, wherein the rod extends through the chamber and is configured to prevent fluid flow to the output channel in the first configuration and to allow fluid flow to output channel in the second configuration. The valve may further include a cam engaging the cam-engaging surface; a pinion fixedly coupled to the cam and comprising a first plurality of gears; a rack comprising a second plurality of gears, wherein the second plurality of gears are configured to mate with the first plurality of gears; and a biasing member coupled to the rod, wherein the biasing member is configured to bias the rod towards the first configuration of the valve. The cam may be pear shaped, the rod may be U-shaped, and the cam-engaging surface may include a wheel. A trigger may be coupled to the rack, wherein actuation of the trigger moves the rod to transition the valve from the first configuration to the second configuration. Movement of the rack in a first direction may be configured to move the pinion and the cam to transition the cam from a first position in which a central longitudinal axis of the cam is substantially parallel to a central longitudinal axis of the rack to a second position in which the central longitudinal axis of the cam is transverse to the central longitudinal axis of the rack; and movement of the rack in a second direction may be configured to move the pinion and the cam from the second position to the first position. The valve may include a chamber, wherein the chamber includes a distal opening fluidically connecting an interior portion of the chamber to the output channel; and a butterfly valve positioned within the distal opening. The butterfly valve may be configured to prevent fluid flow to the output channel in the first configuration of the valve and to allow fluid flow to the output channel in the second configuration of the valve, and rotation of the butterfly valve may move the butterfly valve to transition the valve from the first configuration to the second configuration.

The lumen may be a first lumen and the valve may include a chamber, wherein the chamber includes a distal opening fluidically connecting an interior portion of the chamber to the output channel; and a ball valve positioned within the distal opening and including a second lumen extend through the ball valve. The ball valve may be configured to prevent fluid flow to the output channel in the first configuration of the valve and to allow fluid flow through the second lumen to the output channel in the second configuration of the valve, and rotation of ball valve may transition the ball valve from the first configuration to the second configuration. A housing may include a handle, wherein the handle includes an interior portion configured to receive a fluid container.

A delivery device may be configured to deliver an agent to a target tissue via pressurized fluid. The delivery device may include: a catheter including a lumen, a proximal end, and a distal end; a enclosure configured to store an agent, receive a pressurized fluid, and release a combination of the pressurized fluid and the agent; and a first fluid input upstream of the enclosure. The first fluid input may be configured to release pressurized fluid from a pressurized fluid container toward the enclosure upon coupling the container to the first fluid input. In some examples, the pressurized fluid and agent may flow from the enclosure to the distal end of catheter upon coupling the container to the first fluid input. A total volume of pressurized fluid within the container may be configured to deploy a first amount of the agent through the distal end of the catheter.

In other examples, a method for controlling a fluid delivery to a body of a patient is disclosed. The method may include fluidically connecting a enclosure to a catheter, wherein the enclosure includes an agent within an interior portion of the enclosure and is configured to feed the agent into a lumen of the catheter; moving a distal end of the catheter to a target tissue site, the catheter including a lumen extending longitudinally through the catheter, and wherein the lumen is configured to receive a pressurized fluid from a container through a first input at a position proximally of the enclosure; coupling the container to the first input, wherein the container releases pressurized fluid stored within the container into the first input upon coupling the container to the first input; and contacting an actuator of a valve to open a fluid pathway from the first input to a distal opening of the lumen, causing a fluid and the agent to be released out of the distal end of the catheter. In some examples, the method may further include compressing a spring within the valve assembly; and breaking a fluid seal between an input channel and an output channel of the valve, wherein breaking the fluid seal fluidically connects the first input with the distal opening of the lumen.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. Throughout the drawings, the term "exemplary" is used in the sense of "example," rather than "ideal." The term "distal" refers to a direction away from an operator, and the term "proximal" refers to a direction toward an operator. The term "approximately," or like terms (e.g., "substantially"), includes values+/−10% of a stated value. The term "distal" refers to a portion farthest away from a user when introducing a device into a patient. By contrast, the term "proximal" refers to a portion closest to the user when placing the device into the patient. Proximal and distal directions are labeled with arrows marked "P" and "D", respectively, throughout the figures.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

An agent delivery device may be configured to house an agent at a distal portion of the delivery device and may be configured to control a rate at which an agent and a fluid leave the delivery device at a single location. The delivery device may be configured to house single component agents or multi-component agents. In the case of multi-component agents, the delivery device may be configured to allow for mixing of the components, prior to delivery from the device. Various mechanisms may be utilized in order to pre-pressurize a chamber of the agent and actuate the delivery device to deliver the agent while limiting the number of valves required in the device. These mechanisms may include pneumatics, wires, tubes, valves, or any suitable combination thereof.

Figure 1:
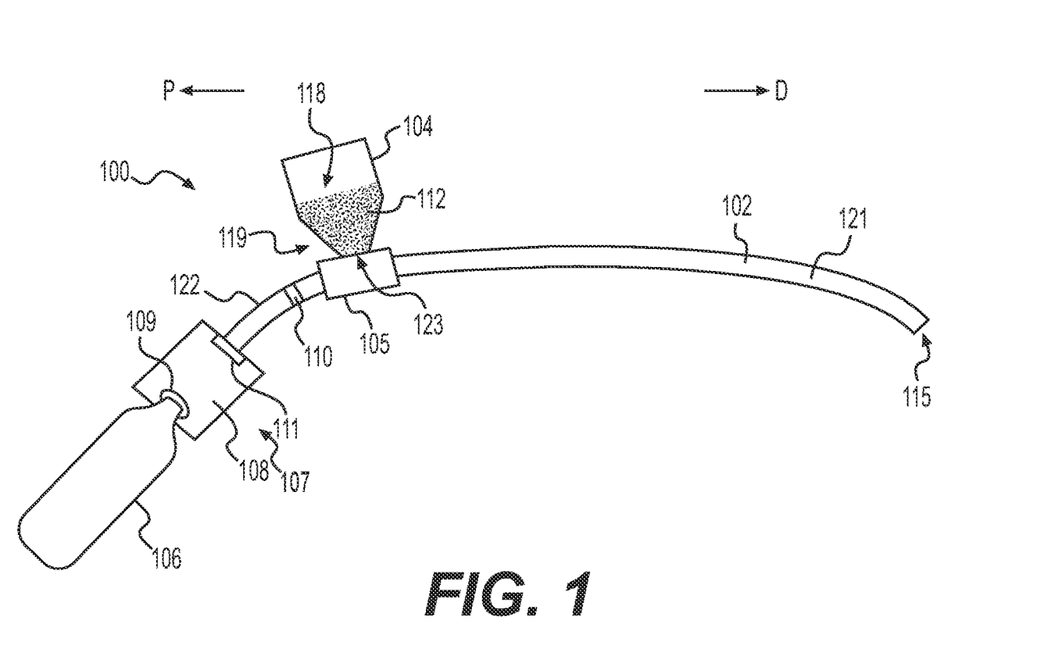
FIG. 1 is a side view of a delivery system according to an exemplary embodiment.

Referring to FIG. 1, a delivery system 100 according to an embodiment is shown. Delivery system 100 may include a catheter 102, a enclosure 104 containing an agent 112, an enclosure adapter 105, a fluid container 106, a regulator 107 including a fluid source input 109, and a filter 110. In some examples, fluid container 106 may release pressurized fluid into regulator 107 when coupled to regulator 107. For example, input port 109 may be configured to pierce fluid container 106 when fluid container 106 is coupled to regulator 107, releasing pressurized fluid into regulator 107.

With reference to FIG. 1, fluid container 106 is configured to contain a fluid, such as a gas, e.g., carbon dioxide or any other gas or other fluid known in the art. While shown as a cylinder, fluid container 106 may be any shape, such as a torpedo-shape, a sphere, or any other shape known in the art and used for storing fluid. For example, fluid container 106 could be a carbon dioxide tank or cylinder typically found in medical settings, such as a hospital, or a smaller, portable cartridge. In some examples, fluid container 106 may be fluidically connected to a fluid source separate from delivery system 100, such as via a fluid catheter that may fluidically connect to a stationary fluid source in an operating room. Fluid container 106 may include one or more outer walls defining one or more inner chambers (not shown), the inner chamber(s) configured to contain the fluid. The walls of fluid container 106 may be formed of any material suitable for containing the fluid, such as but not limited to a metal alloy, a ceramic, or other material known in the art. The fluid contained in the inner chamber of fluid container 106 may be under pressure. Accordingly, the walls are formed of a material and/or a thickness suitable to contain the fluid at a pressure of, for example, at least approximately 1000 pounds per square inch (PSI), or approximately 850 PSI. For example, gases which may be contained in fluid container 106 may include carbon dioxide ($CO_2$) having a vapor pressure of approximately 2,000-8,000 kPa at typical device temperatures, or nitrogen ($N_2$) having a vapor pressure less than 40 MPa at typical device temperatures. It will be understood that these gases are examples and are not limiting to the types of gases contained in fluid container 106.

With continued reference to FIG. 1, fluid container 106 is attached to regulator 107 at regulator input opening 109. Regulator 107 includes a body 108 (including an input opening 109 and an output opening 111, each for communication to external environment). Input opening 109 of regulator 107 may be configured to pierce fluid container 106. Output opening 111 may be configured to fluidically couple to a proximal end of catheter 102. Body 108 of regulator 107 may be any material known in the art, including but not limited to a metal alloy, a ceramic, and/or a resin. Regulator 107 may be configured to change to flow rate of fluid exiting fluid container 106 such that fluid enters a distal portion of catheter 102 at a selected flow rate. In some examples, fluid may enter a distal portion of catheter 102 at a flow rate in the inclusive range of approximately four standard liters per minute to twelve standard liters per minute of fluid flow. In some examples, delivery system 100 may be configured to operate with fluid flowing through a distal portion of catheter 102 at a flow rate in the inclusive range of between approximately five standard liters per minute to ten standard liters per minute. Fluid container 106 may be coupled to regulator 107 via a pull-cord coupling mechanism or a pump mechanism. In some examples, a pull-cord coupling mechanism may be included in system 100 and may include an actuator including a cord and a pin, and the pin may engage a carbon dioxide cartridge (or other fluid cartridge) to release fluid from the cartridge when a user pulls the cord. For example, the pin may puncture the cartridge and result in pressurized fluid flowing in system 100. In other examples, a pump mechanism may be included in system 100 and may be configured to supply pressurized fluid to system 100, for example by supplying pressurized gas in system 100. In some examples, system 100 may not include regulator 107 and container 106 may be coupled directed to catheter 102 via an input opening similar to input opening 109.

A distal portion of catheter 102 (a portion distal to regulator 107) may supply fluid under pressure from fluid container 106 and regulator 107 to enclosure 104 and enclosure adapter 105. Enclosure 104 may be cylindrical and may include an interior cavity 118 and a funnel portion 119 at an end of enclosure 104. Enclosure 104 may be configured to store an agent 112, such as a powder or liquid medicament, within interior cavity 118 and interior cavity 118, may be fluidically connected to adapter 105. Funnel portion 119 may include tapered surfaces forming a portion of interior cavity 118 that lead to an opening 123 at an end of enclosure 104. Funnel portion 119 may be configured to direct agent 112 through opening 123 into adapter 105. In some examples, enclosure 104 may be configured to gravity feed agent 112 into adapter 105. Enclosure 103 may be any suitable material known in the art. In some examples, enclosure 103 may be made of a transparent material.

Opening portion 123 may be configured to couple to adapter 105. Adapter 105 may include an interior cavity (not shown) fluidically connecting three separate openings. Two of the three separate openings may be configured to couple to portions of catheter 102, and one of the three separate openings may be configured to couple to opening 123 of enclosure 104. An opening of adapter 105 may be configured to removably couple to enclosure 104. Adapter 105 may be made of metal, polymer, or any other suitable material known in the art.

Catheter 102 may be cylindrical and may include a lumen extending along its central longitudinal axis. In some examples, catheter 102 may include a proximal portion 122 and a distal portion 121. Proximal portion 122 of catheter 102 may be coupled to adapter 105 and may fluidically connect regulator 107 with adapter 105. Distal portion 121 of catheter 102 may be coupled to adapter 105 at a proximal end of distal portion 121, and distal portion 121 may extend to a distal opening 115. Catheter 102 may be made of any material, for example reinforced rubber or a suitable plastic, that allows catheter 102 to withstand the pressures of the fluid, while simultaneously allowing for unrestricted movement of catheter 102. Distal portion 121 may be flexible and be configured to bend to facilitate movement through a body lumen of a patient, e.g. a gastrointestinal tract. Proximal portion 122 of catheter 102 may include a filter 110 positioned within the lumen of catheter 102. Filter 110 may be configured to allow fluid flow from the regulator 107 distally through the lumen of catheter 102, and may also be configured to prevent movement of agent 112 proximally through catheter 102. In some examples, filter 110 may be configured to restrict fluid flow through catheter 102 by narrowing the diameter of the interior lumen of catheter 102. System 100 may provide a means to deliver agent 112 to a target tissue without the need of any valves within catheter 102, which may reduce procedure time and may simplify a procedure of delivery of an agent 112 to tissue.

In operation, a user may first insert an agent 112 into enclosure 104 of delivery system 100. The user may then position distal opening 115 of catheter 102 proximate to target tissue of a patient, for example target tissue within a body lumen of a patient. Once distal opening 115 is positioned proximate to or at the target tissue, the user may couple fluid container 106 to regulator 107. By coupling fluid container 106 to regulator 107, input port 109 may pierce or otherwise initiate fluid flow from fluid container 106 through regulator 107 and into catheter 102. Fluid may then flow from regulator 107 through proximal portion 122 of catheter 102 and into adapter 105 and enclosure 104. When fluid flows into adapter 105 and enclosure 104, agent 112 may be moved in the direction of fluid flow and carried through catheter 102 to distal opening 115. Agent 112 may then be deployed through distal opening 115 and propelled towards the target tissue via the fluid flow. Since the fluid flow is initiated when fluid container 106 is coupled to regulator 108, a user does not need to actuate a valve or otherwise adjust the deployment of agent via fluid flow from fluid container 106. The actuation of system 100 through coupling fluid container 106 to regulator 107 (for example, piercing a carbon dioxide container by coupling it to regulator 107) provides a means to deliver agent 112 to target tissue without the need for valving and produces a single shot of agent 112 to target tissue. For example, system 100 may be configured to receive a single shot of pressurized fluid supplied by fluid container 106, such as a specific volume of carbon dioxide released from fluid container 106 in order to deliver a specific amount of agent 112 to distal opening 115. By providing the user with a device that may deliver a measured amount of agent by connecting a fluid container 106 with a specific amount of fluid, additional steps of actuating a valve assembly or selectively releasing liquid into a device via an actuator may be eliminated, and may save the user time during an operation. In some examples, system 100 may not include regulator 107. In some examples, all of or the majority of agent 112 may be moved out of enclosure 104 when fluid container 106 is coupled to regulator 108, e.g., each enclosure 104 may be a single dosage of a therapeutic agent. The volume of fluid enclosure 106 may be configured to deploy a selected amount of agent 112 using system 100.

Figure 2:
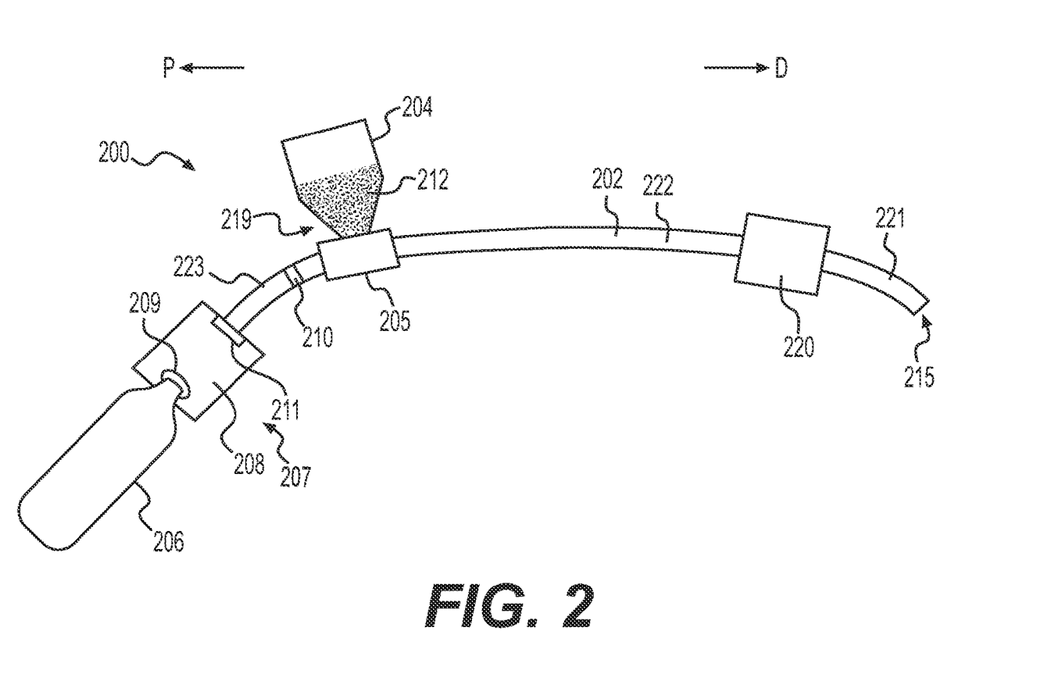
FIG. 2 is a side view of a delivery system according to an exemplary embodiment.

FIG. 2 shows an alternative embodiment of a delivery system 200 substantially similar to delivery system 100. Delivery system 200 may include catheter 202 including distal portion 222, proximal portion 223, and distal opening 215; adapter 205; fluid container 206; regulator 207 including regulator body 208, regulator input opening 209 and output opening 211; enclosure 204; agent 212; and filter 210. Any of the features described herein above regarding delivery system 100 may be included in delivery system 200. Delivery system 200 may also include a valve 220 at a distal portion of catheter 202, e.g. any portion of catheter 202 distal of adapter 205. Valve 220 may be fluidically connected to an interior lumen of catheter 202. In some examples, valve 220 may be coupled to distal portion 222 of catheter 202 and a distalmost portion 221 of catheter 202. In other examples, valve 220 may be just distal of adapter 205.

In operation, a user may first couple fluid container 206 to regulator 207 to pressurize delivery system 200 with pressurized fluid, such as pressurized carbon dioxide. Delivery system 200 may be configured to withstand cylinder pressure with valve 220 keeping the fluid pressure and agent 212 contained within delivery system 200. Once delivery system 200 has been pressurized with fluid by coupling fluid container 206 to regulator 207, the user may then selectively release the pressurized fluid and agent 212 from delivery system 200 by actuating valve 220. In some examples, actuation of valve 220 may result in release of fluid and/or agent 212 through distalmost portion 221 of catheter 202 and out of distal opening 215. By providing valve 220 at a distal portion of catheter 202, a user may selectively delivery agent 212 to a target tissue and may allow the user to deliver agent 212 multiple times to the same target area or different target areas. Valve 220 may have any number of mechanisms for regulating the release of fluid from delivery system 200 which are discussed herein below.

Figure 3A:
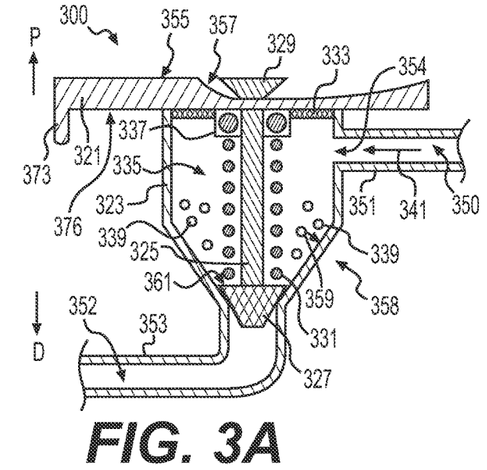
FIGS. 3A and 3B are cross-sectional views of a valve assembly in first and second configurations, respectively, according to an exemplary embodiment.
Figure 3B:
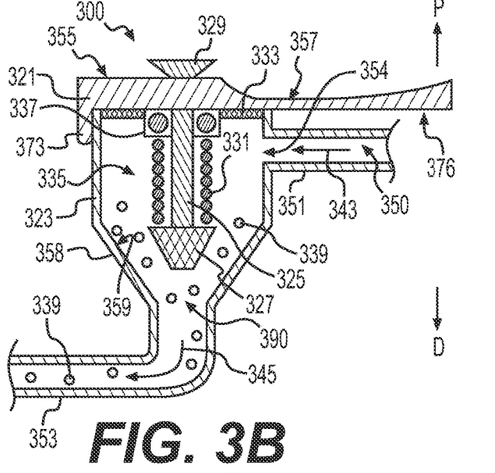

FIGS. 3A and 3B show cross-sectional views of an exemplary valve assembly 300. Valve assembly 300 may be used as valve 220 in FIG. 2. Valve assembly 300 may be configured to operate under a constant fluid pressure feed into input channel 351. Valve assembly 300 may include a valve chamber 323, an input channel 351 including input lumen 350, an output channel 353 including output lumen 352, a rod 325 including a plunger 327 at a distal end of rod 325, a biasing member 331, and a slide 321. Valve assembly 300 may be contained within a holding apparatus (not shown) that may be any suitable shape. For example, valve assembly 300 may be incorporated into a handle for a user to hold during operation (shown in FIG. 8).

Chamber 323 may be cylindrical and may include a cover portion 333 at a proximal end of chamber 323 and a distal opening 390 fluidically connecting chamber 323 with output channel 353. Chamber 323 may include a tapered distal portion 358 with a conical interior surface 359 tapering towards a central longitudinal axis of chamber 323 and towards distal opening 390. Input channel 351 may be cylindrical and may fluidically connect to chamber 323 at an opening 354 at a proximal portion of chamber 323. In some examples, distal portion 222 of catheter 202 (shown in FIG. 2) may be fluidically coupled to input channel 351, and distalmost portion 221 of catheter 202 (shown in FIG. 2) may be fluidically coupled to output channel 353. Input channel 351 may be positioned above output channel 353 to facilitate fluid flow (such as by allowing gravity to exert force onto the fluid to push the fluid towards output channel 353) from input channel 351 through chamber 323 to output channel 353.

Rod 325 may be cylindrical and may extend through chamber 323. In some examples, rod 325 may extend along a central longitudinal axis of chamber 323. Plunger 327 may be coupled to a distal end of rod 325. Plunger 327 may be conical and may extend radially-outward from a central longitudinal axis of rod 325. In some examples, rod 325 may be tapered such that the distance between a central longitudinal axis of rod 325 and the radially-outer surface of plunger decreases as plunger 327 extends distally. Plunger 327 may be rubber, hard plastic, or any other suitable material known in the art. Plunger 327 may be configured to form a fluid-tight seal with chamber 323 at distal opening 390. In some examples, rod 325 may be configured to translate distally within chamber 323 until plunger 327 contacts an interior surface of chamber 323 and forms a fluid tight seal preventing fluid from flowing through distal opening 390. Proximal end 329 of rod 325 may be tapered and may extend radially outward from a central longitudinal axis of rod 325 as proximal end 329 extends proximally. Rod 325 may extend through an opening 371 (shown in FIGS. 4A and 4B) in slider 321 and also through an opening in cover 333. Proximal end 329 of rod 325 may be tapered so as to prevent rod 325 from moving through opening 371. Rod 325 may move proximally (up in the Figures) through opening 371, such as when proximal end 329 is translated along a proximally-facing surface 355, 357 of slider 321.

Biasing member 331 may extend circumferentially around rod 325 and may be coupled to cover 333 via a coupler 337. Coupler 337 may fixedly couple a proximal end of biasing member 331 to cover 333. A distal end of biasing member 331 may be fixedly coupled to plunger 327 and may contact a proximal-facing surface 361 of plunger 327. In some examples, biasing member 331 may be a spring. Rod 325 may extend through a central longitudinal axis of biasing member 331. Biasing member 331 may exert a force on rod 325 pushing rod 325 towards distal opening 390. In an extended state (shown in FIG. 3A), biasing member 331 may exert a force on rod 325 such that plunger 327 forms a fluid tight seal with an interior surface of chamber 323, preventing fluid flow through distal opening 390. In a retracted state (shown in FIG. 3B), biasing member 331 may exert a force on rod 325 pushing rod distally towards distal opening 390. Proximal end 329 of rod 325 may contact slider 321 and counteract the force exerted on rod 325 from biasing member 331. In some examples, when a user transitions proximal end 329 from a position contacting first portion 355 of slider 321 to a position contacting second portion 357 of slider 321, proximal end 329 may slide across second portion 357, and rod 325 may move distally towards distal opening 390 via a force exerted on rod 325 from biasing member 331.

Figure 4A:
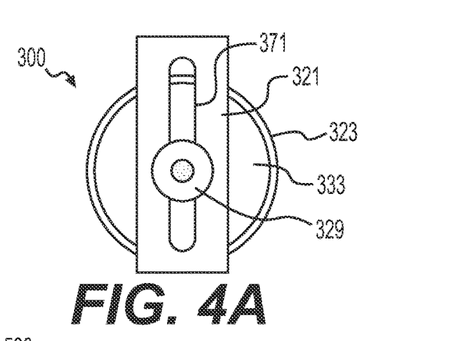
FIGS. 4A and 4B are top views of a valve assembly in first and second configurations, respectively, according to an exemplary embodiment.
Figure 4B:
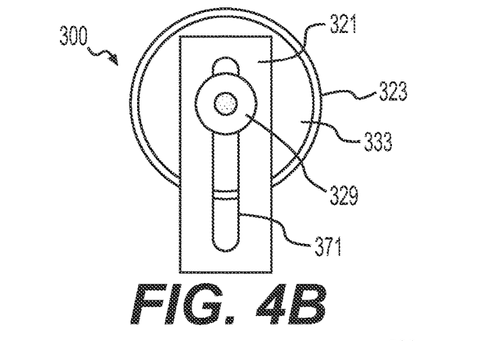

Slider 321 may extend across cover 333 and across a proximal portion of chamber 323. Slider 321 may be rectangular or any other suitable geometric shape. A proximal facing surface of slider 321 may include a first portion 355 and a second portion 357. In some examples, first portion 355 may be planar and second portion 357 may be curved. Slider 321 may vary in thickness with a larger thickness at a portion of slider 321 including the first portion 355 and a smaller thickness at a portion of slider 321 including a second portion 357. For example, slider 321 may extend outward from a central longitudinal axis of slider 321 as slider 321 extends from the second portion 357 to the first portion 355. A distal facing surface 376 of slider 321 may be planar and may be configured to slide across cover 333 and/or a proximal end of chamber 323. FIGS. 4A and 4B are top views of valve assembly 300 showing chamber 323, cover 333, proximal end 329 of rod 325, and slider 321 including opening 371. FIG. 4A corresponds to the position of valve assembly 300 shown in FIG. 3A, and FIG. 4B corresponds to the position of valve assembly 300 shown in FIG. 3B. Slider 321 may be designed with a slope of second portion 357 such that when slider 321 is translated from a position in which proximal end 329 moves from a position contacting first portion 355 to a position contacting second portion 357, biasing member 331 returns rod 325 to a closed position, which may facilitate dosing of agent 339.

Slider 321 is configured to translate transverse to the central longitudinal axis of rod 325 and is configured to move rod 325 in a proximal direction or a distal direction (up or down in the Figures). As slider 321 moves in a direction transverse to the longitudinal axis of rod 325, proximal end 329 slideably engages proximal facing surfaces 355, 357 of slider 321. For example, a user may transition valve assembly 300 from a first state shown in FIGS. 3A and 4A to a second state shown in FIGS. 3B and 4B by translating slider across cover 333 such that proximal end 329 slides across second portion 357 to first portion 355, and thus forcing rod 325 to move proximally via the interaction between proximal end 329 and proximally facing surfaces 355, 357 of slider 321. In some examples, slider 321 may include a flange 373 extending radially outward from a longitudinal axis of slider 321. Flange 373 may be configured to prevent movement of slider 321 across cover 333 once flange 373 engages an exterior surface of chamber 323. FIG. 3B shows an example of a position of valve assembly 300 in which flange 373 engages an exterior surface of chamber 323. Slider 321 may be configured to couple to an actuator to facilitate movement of slider 321 to actuate valve assembly 300. For example, slider 321 may be coupled to a trigger assembly (such as a trigger similar to trigger 574 shown in FIGS. 5A, 5B, and 8).

In operation, a user may operate valve assembly 300 while operating delivery system 200, with valve assembly 300 serving as valve 220 shown in FIG. 2. Once a fluid container 206 is coupled to input 209 and supplies pressurized fluid to delivery system 200, a user may actuate valve assembly 300 to selectively release agent 339 through valve assembly 300. For example, a user may translate slider 321 in a first direction to transition valve assembly from a closed state (shown in FIG. 3A) to an open state (shown in FIG. 3B) to release agent 339 through output channel 353 to be delivered to target tissue of a patient. Agent 339 may be moved from container 204, through catheter 202, and into valve assembly 300, and output through output channel 353 for delivery to distal opening 215. Agent 339 may be moved by a force applied to agent 339 via pressurized fluid supplied by fluid container 206. To stop the release of agent 339 through output channel 353, a user may translate slider 321 in a second direction opposite the first direction to move proximal end 329 from a position contacting first portion 355 of a proximally-facing surface of slider 321 to a position contacting second portion 357 of a proximally-facing surface of slider 321, thus allow biasing member 331 to move rod 325 distally and move plunger 327 into a position fluidically sealing distal opening 390. Once plunger 327 is at a position fluidically sealing distal opening 390, fluid flow (shown as arrow 341, 343 and 345 in FIGS. 3A and 3B) is prevented from reaching output channel 353. In some examples, the user may transition slider 321 from the position shown in FIG. 4B to the position shown in FIG. 4A to stop the release of agent 339 from output channel 353.

Figure 5A:
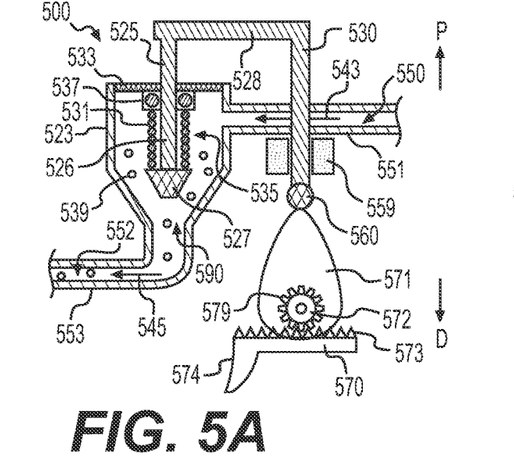
FIGS. 5A and 5B are cross-sectional views of a valve assembly in first and second configurations, respectively, according to an exemplary embodiment.
Figure 5B:
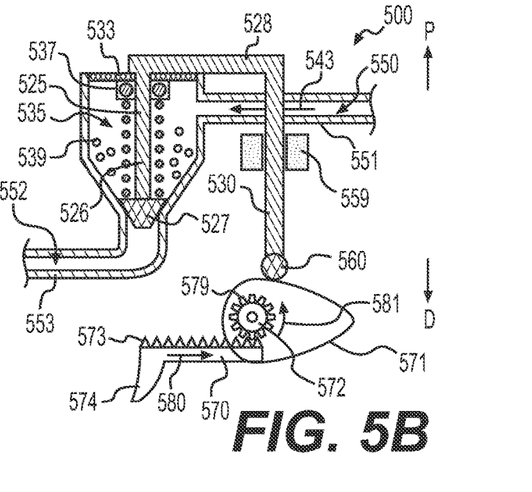

FIGS. 5A and 5B show an alternative embodiment of a valve assembly 500 that utilizes a cam and follower mechanism to actuate the valve assembly 500. Valve assembly 500 may be used as valve 220 in FIG. 2. In some examples, valve assembly 500 may be configured to operate under a constant fluid pressure feed into an input channel 551. Valve assembly 500 may include a valve chamber 523, an input channel 551 including input lumen 550, an output channel 553 including output lumen 552, a rod 525 including a plunger 527 at a distal end of rod 525, a biasing member 531, a cover 533, and a coupler 537. Any of the components of valve assembly 500 may have any of the attributes and/or characteristics of components of valve assembly 300. Valve assembly 500 may be contained within a holding apparatus (not shown) that may be any suitable shape. For example, valve assembly 500 may be incorporated into a handle for a user to hold during operation (shown in FIG. 8).

Rod 525 may include a first portion 526, a second portion 528, a third portion 530, and a wheel 560 at a distal end of third portion 530. Each of first portion 526, second portion 528, and third portion 530 may be rigid and cylindrical or any other suitable shape. In some examples, wheel 560 may be rotatable relative to third portion 530. In other examples, wheel 560 may be fixedly coupled to third portion 530, may be configured to slidably engage cam 571, and may not rotate. Although third portion 530 and input channel 551 are both shown in cross-section, third portion 530 is in a different plane than input channel 551 such that third portion 530 and input channel 551 do not intersect, but extend transverse to each other. First portion 526 may extend from plunger 527, through an opening in cover 533, to a position proximal to cover 533. First portion 526 may be fixedly coupled to second portion 528, and, in some examples, second portion may extend transverse to first portion 526. In some examples, second portion 528 may have a central longitudinal axis perpendicular to a central longitudinal axis of first portion 526 and/or a central longitudinal axis of third portion 530. Second portion 528 may be fixedly coupled to third portion 530 at a first end, and may be fixedly coupled to first portion 526 at a second end opposing the first end. Third portion 530 may extend distally from a first end to a second end, with the second end of third portion 530 coupled to wheel 560. In some examples, a central longitudinal axis of third portion 530 may be parallel to a central longitudinal axis of first portion 526. In some examples, first portion 526, second portion 528, and third portion 530 may form a U-shape. Third portion 530 may be held by a bracket 559 coupled to a housing (not shown) containing valve assembly 500. Bracket 559 may allow proximal and distal movement of third portion 530, and may prevent lateral movement transverse to the proximal and distal directions. In some examples, bracket 559 may be integrally formed with and/or fixedly coupled to housing 840 (shown in FIG. 8).

Cam 571 may be fixedly coupled to a pinion 572. Cam 571 may be pear shaped (shown in FIGS. 5A and 5B), snail shaped, circular with a pinion coupled at an off-center position, or any other suitable shape, and may be made of any suitable material known in the art. Pinion 572 may be cylindrical, and may be rotatably coupled to a housing (not shown) containing valve assembly 500. Pinion 572 may include gears (teeth) 579, and rotation of pinion 572 may result in rotation of cam 571. Gears 579 may be configured to mate with gears (teeth) 573 of rack 570. Rack 570 may be coupled to an actuator for translating rack 570 to move gears 573, such as trigger 574 shown in FIGS. 5A and 5B. Alternatively, rack 570 could be actuated via a button, lever, electronically controlled motor, or any other means known in the art. In some examples, movement of rack 570 via actuation of trigger 574 may engage gears 573 with gears 579, and thus may cause rotation of pinion 572 and cam 571. A central longitudinal axis of rack 570 may extend transverse to an axis of rotation of pinion 572. In some examples, rotation of pinion 572 via rack 570 may transition cam 571 from a position in which a central longitudinal axis of cam 571 is transverse to a central longitudinal axis of third portion 530 (FIG. 5A) to a position in which a central longitudinal axis of cam 571 is aligned with a central longitudinal axis of third portion 530 (FIG. 5B).

In operation, a user may actuate rack 570 in order to open valve assembly 500 and release agent 539 to a distal opening 215 of catheter 202 (shown in FIG. 2). After fluid container 206 is coupled to regulator 207, pressurized fluid may flow into input channel 551 and chamber 523. In a closed configuration (shown in FIG. 5B), plunger 527 prevents fluid flow through distal opening 590. To open valve assembly 500, the user may actuate rack 570, for example by pushing on trigger 574. By pushing on trigger 574, gears 573 of rack 570 may engage gears 590 of pinion 572, rotating pinion 572 and cam 571. As cam 571 rotates, wheel 560 engages the exterior surface of cam 571, and cam 571 pushes rod 525 proximally. By pushing rod 525 proximally, plunger 527 disengages with the interior surface of chamber 523 and allows fluid to flow through distal opening 590. When the user releases trigger 574, biasing member 531 may move rod 525 distally and return valve assembly 500 to a closed position (FIG. 5B).

Figure 6A:
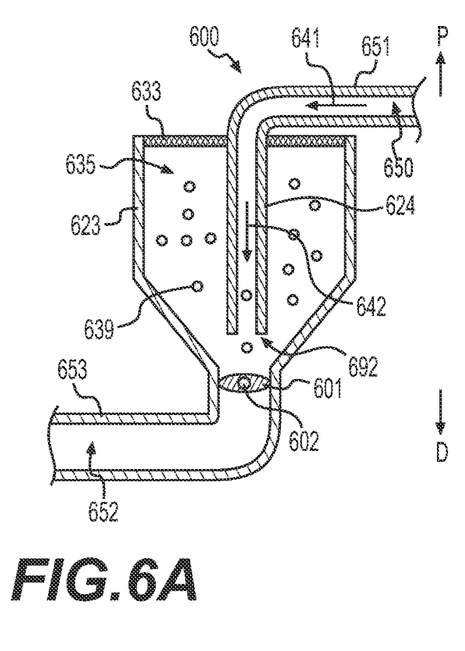
FIGS. 6A and 6B are cross-sectional views of a valve assembly in first and second configurations, respectively, according to an exemplary embodiment.
Figure 6B:
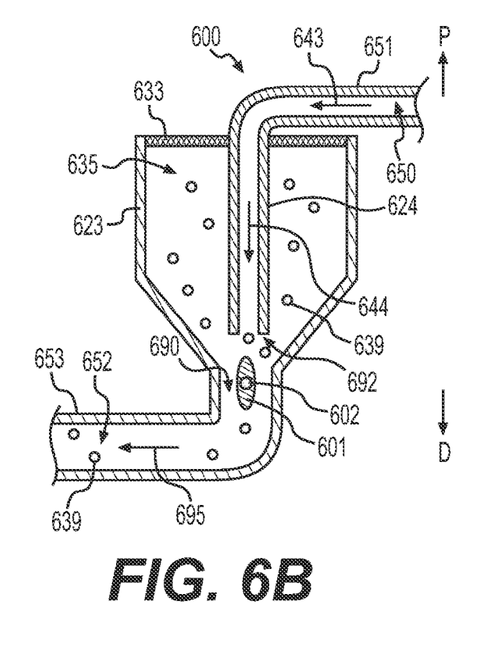

FIGS. 6A and 6B show an alternative embodiment of a valve assembly 600. Valve assembly 600 may be used as valve 220 in FIG. 2. Valve assembly 600 may include a valve chamber 623 including interior portion 635, an input channel 651 including input lumen 650, an output channel 653 including output lumen 652, a cover 633, and a butterfly valve 601. Any of the components of valve assembly 600 may have any of the attributes and/or characteristics of components of valve assemblies 300 and 500. Valve assembly 600 may be contained within a holding apparatus (not shown) that may be any suitable shape. For example, valve assembly 600 may be incorporated into a handle for a user to hold during operation (shown in FIG. 8). In some examples, valve assembly 600 may be configured to operate under a constant fluid pressure feed into input channel 651.

Input channel 651 may extend through an opening in cover 633 and within chamber 623. For example, a distal portion 624 of input channel 651 may extend along a central longitudinal axis of chamber 623 and a distal end 692 of input channel 651 may, in some examples, be positioned directly above (proximal to) distal opening 690. Butterfly valve 601 may be oval shaped, or may be any other suitable shape. Butterfly valve 601 may be configured to extend across distal opening 690 so as to prevent fluid flow (shown as arrows 641, 642 in FIG. 6A) through distal opening 690 and into lumen 652 of output channel 653. Butterfly valve 601 may include a pivot rod 602, and butterfly valve 601 may pivot about pivot rod 602. In some examples, pivot rod 602 may be configured to be actuated by a user by rotating pivot rod 602 to move butterfly valve 601. In other examples, valve assembly 600, and in some embodiments a butterfly valve 601, may be actuated via a trigger rack and pinion, by gas flow, by a manual twist action, or a by pneumatic liquid/gas system. In some examples, actuating valve assembly 600 to transition valve assembly 600 from a closed to an open configuration may require rotation of butterfly valve 601 ninety degrees. FIG. 6A shows valve assembly 600 in a closed configuration in which fluid flow, illustrated by arrows 641, 642, flows into chamber 623 but is prevented from flowing into lumen 652 of output channel 653. When valve assembly 600 is in a closed configuration as shown in FIG. 6A, butterfly valve 601 spans across distal opening 690 and seals distal opening 690, preventing fluid flow into output channel 653. In a closed configuration, a longitudinal axis of butterfly valve 601 may extend across distal opening 690. When valve assembly 600 is in an open configuration as shown in FIG. 6B, butterfly valve 601 is positioned to allow fluid flow through distal opening 690, and thus allow agent 639 to flow through output channel 653, illustrated by arrows 643, 644, 695. For example, in an open configuration, a longitudinal axis of butterfly valve 601 may align with a longitudinal axis or distal portion 624 or a longitudinal axis of chamber 623. A user may rotate pivot rod 602 to transition valve assembly 600 from a closed configuration to an open configuration, and vice versa.

Figure 7A:
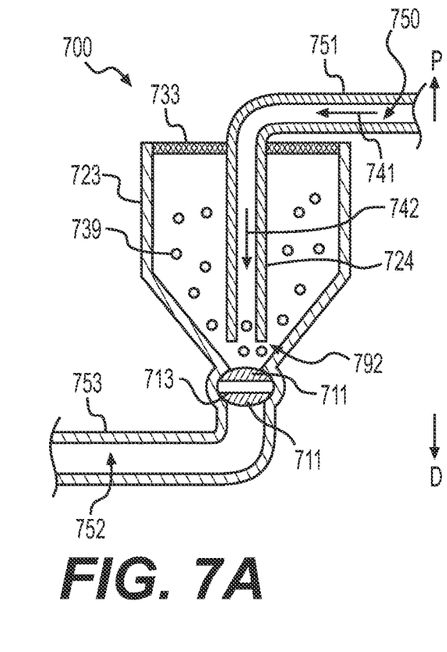
FIGS. 7A and 7B are cross-sectional views of a valve assembly in first and second configurations, respectively, according to an exemplary embodiment.
Figure 7B:
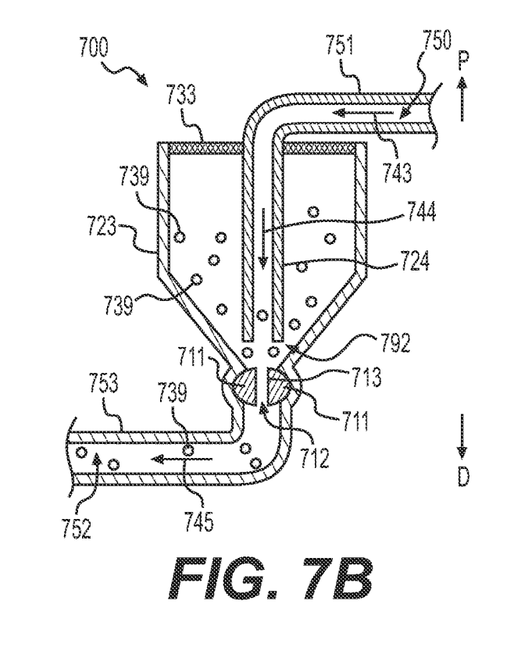

FIGS. 7A and 7B show another alternative embodiment of a valve assembly 700. Valve assembly 700 may be used as valve 220 in FIG. 2. Valve assembly 700 may include a valve chamber 723, an input channel 751 including input lumen 750 and distal end 792, an output channel 753 including output lumen 752, a cover 733, and a ball valve 711. Any of the components of valve assembly 700 may have any of the attributes and/or characteristics of components of valve assemblies 300, 500, and 600. Valve assembly 700 may be contained within a holding apparatus (not shown) that may be any suitable shape. For example, valve assembly 700 may be incorporated into a handle for a user to hold during operation (shown in FIG. 8). In some examples, valve assembly 700 may be configured to operate under a constant fluid pressure feed into input channel 751.

Ball valve 711 may be configured to extend across distal opening 712 so as to prevent fluid flow (shown as arrow 741, 742 in FIG. 7A) through distal opening 712 and into lumen 752 of output channel 753. Ball valve 711 may be spherical and may include a lumen 713 extending through ball valve 711. In some examples, ball valve 711 may include a pivot rod (not shown), and ball valve 711 may pivot about pivot rod. In some examples, actuation of a pivot rod may rotate ball valve 711. FIG. 7A shows valve assembly 700 in a closed configuration in which fluid flow, illustrated by arrows 741, 742, flows into chamber 723 but is prevented from flowing into lumen 752 of output channel 753. When valve assembly 700 is in a closed configuration as shown in FIG. 7A, ball valve 711 spans across distal opening 712 and seals distal opening 712, preventing fluid flow into output channel 753. In a closed configuration, a longitudinal axis of lumen 713 may extend across distal opening 712, and an interior surface of chamber 723 may cover each end of lumen 713. When valve assembly 700 is in an open configuration as shown in FIG. 7B, ball valve 711 is positioned to allow fluid flow, illustrated by arrows 743, 744, 745, through lumen 713 and distal opening 712, and thus allow agent 739 to flow through output channel 753. For example, in an open configuration, a longitudinal axis of lumen 713 may align with a longitudinal axis of distal portion 724 of input channel 751 or a longitudinal axis of chamber 723. A user may rotate ball valve 711 to transition valve assembly 700 from a closed configuration to an open configuration, and vice versa. In some examples, actuating valve assembly 700 to transition valve assembly 700 from a closed to an open configuration may require rotation of ball valve 711 ninety degrees. Valve assembly 700, and in some embodiments a ball valve 711, may be actuated via a trigger rack and pinion, by gas flow, by a manual twist action, a by pneumatic liquid/gas system, or by any other method known in the art.

Figure 8:
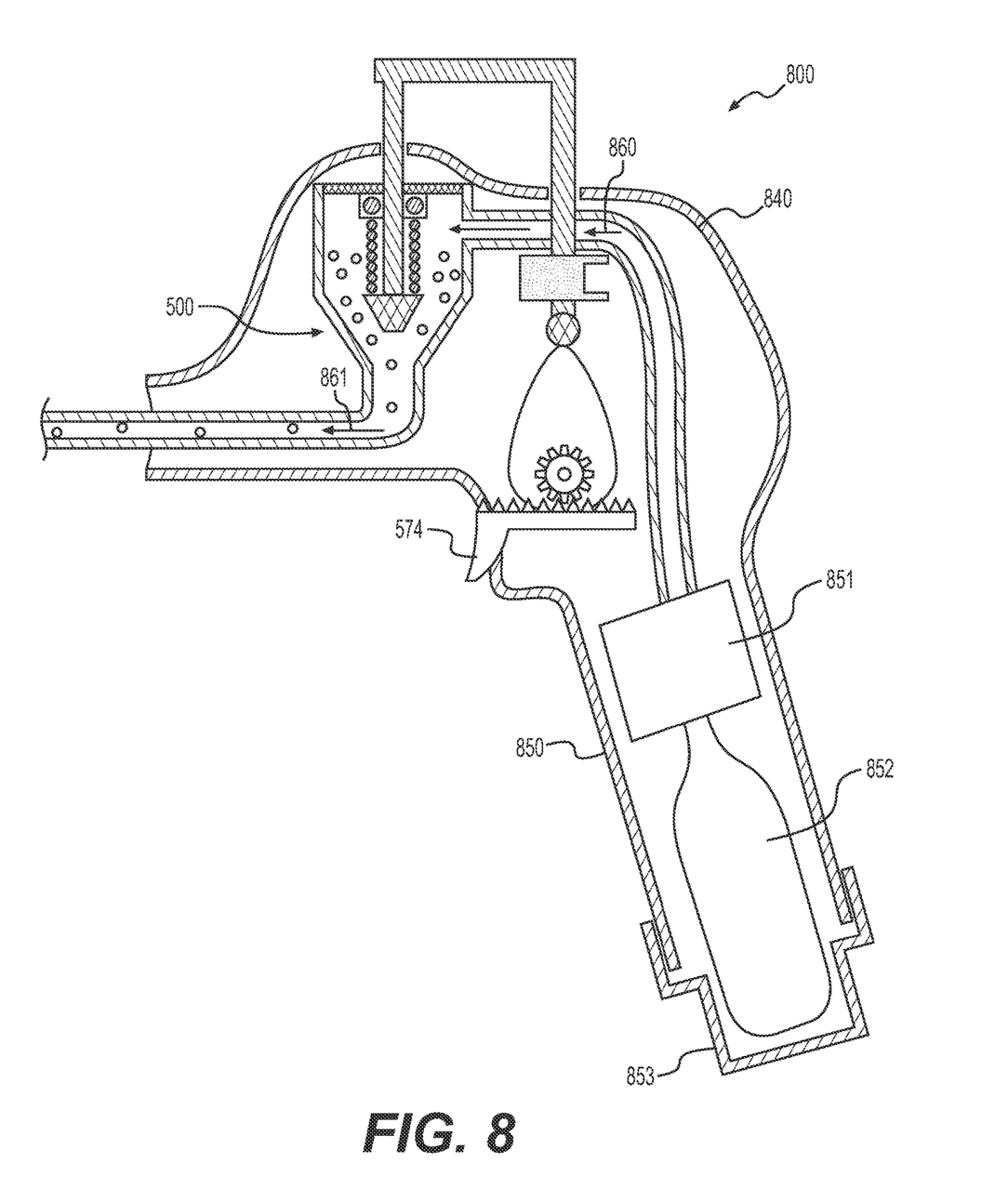
FIG. 8 is a cross-sectional side view of a handle assembly including a valve assembly, according to an exemplary embodiment.

FIG. 8 shows a side cross-sectional view of an exemplary housing 840 containing valve assembly 500. Housing 840 may include a handle portion 850 configured for a user to hold housing 840. In some examples, handle portion 850 may be configured to enclose a regulator 851 and/or a fluid container 852. A user may access an interior portion of handle portion 850 via a cap 853 removably coupled to a portion of handle portion 850. A trigger 574 may extend outward from housing 840 to allow a user to actuate trigger 574. Pressurized fluid may flow (shown as arrows 860, 861) from fluid container 852, through regulator 851, and into valve assembly 500. Any of the valve assemblies 300, 500, 600, 700 disclosed herein may be incorporated into housing 840. By providing a handle portion 850, housing 840 may facilitate the use of valve assembly 300, 500, 600, 700 and provide a more ergonomic way for a user to hold and actuate a valve assembly 300, 500, 600, 700.

Unless described otherwise, the structural elements of valve assemblies 300, 500, 600, 700 may be any material known in the art, including but not limited to a metal alloy, a ceramic, and/or a resin.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. A device configured to deliver an agent to a target tissue via a pressurized fluid, the device comprising:
    a catheter including a lumen;
    an enclosure configured to store an agent, receive a pressurized fluid, and release a combination of the pressurized fluid and the agent; and
    a valve defining a chamber positioned downstream of the enclosure to receive the combination of the pressurized fluid and the agent from the enclosure, the valve having a plunger and a rod that are configured to translate relative to the chamber between:
        a first configuration in which the plunger is moved into contact with an internal surface of the chamber, thereby preventing a flow of the combination through the lumen such that the agent received within the valve from the enclosure is collected inside the chamber of the valve; and
        a second configuration in which the plunger is moved out of contact with the internal surface of the chamber, thereby permitting the flow of the combination through the lumen such that the agent that is collected within the chamber is released from the valve;
        wherein the plunger is coupled to the rod inside the chamber, and the rod extends at least partially out of the chamber and through a slider that is slidably coupled to the chamber.

2. The device according to claim 1, further comprising a first fluid input configured to release pressurized fluid from a pressurized fluid container into the lumen upon coupling the container to the first fluid input.

3. The device according to claim 1, wherein the valve is within a housing, and the internal surface of the chamber is conical to define a tapered distal portion of the valve, and wherein the tapered distal portion is configured to guide the agent that is stored inside the chamber of the valve when in the first configuration outwards towards the lumen when moved towards the second configuration;
    wherein the plunger includes a conical configuration that is configured to interface with the internal surface of the chamber to form a seal between the plunger and the tapered distal portion of the valve when in the first configuration; and
    wherein the housing includes a handle.

4. The device according to claim 1, wherein the agent is a powdered medicament.

5. The device according to claim 1, wherein the chamber is fluidically connected to the lumen via an output channel;
    wherein the valve includes the rod including the plunger at a distal end of the rod, wherein the rod extends through the chamber and is configured to prevent the flow to the output channel in the first configuration and to allow the flow to the output channel in the second configuration;
    the slider including a slot, wherein the rod extends out of the chamber and through the slot, and wherein the slider is configured to transition the valve from the first configuration to the second configuration by movement of the slider, thereby pulling the rod relatively upwards through the slot that is formed in the slider; and
    a biasing member coupled to the rod, wherein the biasing member is configured to bias the rod towards the first configuration of the valve, thereby pulling the rod relatively downwards through the slot.

6. The device according to claim 5, wherein the slider includes a slide on which the rod rests, the slide having a first portion including a curved surface and a second portion including a planar surface, the rod is configured to slide across each of the curved surface and the planar surface of the slide in response to translating relative to the chamber between the first configuration and the second configuration.

7. The device according to claim 6, wherein the rod includes an end positioned outside of the chamber and extending radially outward relative to an adjacent portion of the rod that is disposed inside the chamber, and wherein the end of the rod prevents the rod from moving relatively downwards through the slot of the slider when the end of the rod contacts the curved surface of the first portion of the slide.

8. The device according to claim 7, wherein the end of the rod slidably engages the slider along the curved surface of the first portion when in the first configuration and the planar surface of the second portion when in the second configuration.

9. The device according to claim 1, further comprising a housing including a handle, wherein the handle includes an interior portion configured to receive a pressurized fluid container.

10. A device configured to deliver an agent via a pressurized fluid, the device comprising:
  a catheter including a lumen;
  an enclosure configured to store the agent, receive the pressurized fluid, and release a combination of the pressurized fluid and the agent; and
  a valve in fluid communication with the catheter and the enclosure, wherein the valve is configured to receive the agent from the enclosure, the valve including a plunger, a slider, and a rod coupled to each of the plunger and the slider on opposing ends of the rod, wherein the rod extends through a portion of the slider such that the rod is movable through the slider;
  wherein the slider of the valve is urged towards a first configuration in which the plunger and the rod of the valve are positioned relative to the catheter to prevent a flow of the combination of the pressurized fluid and the agent outwards through the valve and into the lumen, such that the agent is maintained inside the valve, and
  wherein the slider of the valve is movable towards a second configuration in which the plunger and the rod of the valve are positioned relative to the catheter to permit the flow of the combination of the pressurized fluid and the agent out through the valve and into the lumen in response to counteracting a force urging the valve towards the first configuration.

11. The device according to claim 10, wherein the valve includes a chamber, wherein the rod and the plunger are disposed inside the chamber such that the rod and the plunger are configured to translate relative to the chamber when the valve transitions between the first configuration and the second configuration.

12. The device according to claim 11, wherein the plunger is configured to contact an internal surface of the chamber to prevent the flow of the combination of the agent and the pressurized fluid out of the chamber and into the lumen when the valve is in the first configuration; and
  wherein the plunger is tapered radially outwards and the internal surface of the chamber is tapered radially inwards to (i) interface with the plunger when in contact with one another while the valve is in the first configuration and (ii) to guide the agent that is maintained inside the chamber out of the valve and into the lumen when the valve is moved towards the second configuration.

13. The device according to claim 12, wherein the plunger is separated from the internal surface of the chamber to permit the flow of the combination out of the chamber and into the lumen when the valve is in the second configuration.

14. The device according to claim 13, wherein the valve includes the rod having a distal end disposed inside the chamber and a proximal end disposed outside of the chamber, and the plunger is positioned at the distal end of the rod.

15. The device according to claim 14, wherein the rod is biased to a first position such that the distal end inside the chamber with the plunger is moved into contact with the internal surface and the proximal end outside the chamber is moved into contact with a first surface of the slider, thereby urging the valve towards the first configuration.

16. The device according to claim 15, wherein the rod is biased to a second position such that the distal end inside the chamber with the plunger is moved relatively away from the internal surface and the proximal end outside the chamber is moved into contact with a second surface of the slider, thereby moving the valve towards the second configuration.

17. The device according to claim 16, wherein the valve includes a biasing member coupled to the rod, and wherein the biasing member is configured to bias the rod to the first position.

18. A device configured to deliver an agent, the device comprising:
  a container for storing a pressurized fluid;
  an enclosure for storing the agent;
  a valve including a chamber for receiving a combination of the pressurized fluid from the container and the agent from the enclosure; and
  a slider configured to move relative to the chamber;
  a rod configured to move through the slider and relative to the chamber from a first position to a second position in response to the movement of the slider; and
  a plunger configured to move relative to the chamber from the first position to the second position;
  wherein, when in the first position, the plunger is urged into contact with an internal surface of the chamber to seal the combination of the pressurized fluid and the agent inside the chamber in response to the rod moving relatively downwards through the slider, thereby preventing the combination of the pressurized fluid and the agent from exiting the valve;
  wherein, in the second position, the plunger is not in contact with the internal surface of the chamber such that the combination of the pressurized fluid and the agent is not sealed inside the chamber in response to the rod moving relatively upwards through the slider, thereby permitting the combination of the pressurized fluid and the agent to exit the valve.

19. The device according to claim 18, wherein the valve includes the rod disposed inside the chamber and the plunger is positioned at an end of the rod;
  wherein the rod is biased to the first position inside the chamber and moved relatively downwards through the slider with the plunger abutting against the internal surface.

20. The device according to claim 19, wherein the rod is biased to the second position inside the chamber and moved relatively upwards through the slider with the plunger separated form the internal surface.

* * * * *